(12) United States Patent
Scheid et al.

(10) Patent No.: US 8,781,209 B2
(45) Date of Patent: *Jul. 15, 2014

(54) SYSTEM AND METHOD FOR DATA-DRIVEN AUTOMATED BORESCOPE INSPECTION

(75) Inventors: Paul Raymond Scheid, West Hartford, CT (US); William J. Welch, Madison, CT (US); Alan Matthew Finn, Hebron, CT (US); Hongcheng Wang, Vernon, CT (US); Ziyou Xiong, Wethersfield, CT (US)

(73) Assignee: United Technologies Corporation, Hartford, CT (US)

( * ) Notice: Subject to any disclaimer, the term of this patent is extended or adjusted under 35 U.S.C. 154(b) by 154 days.

This patent is subject to a terminal disclaimer.

(21) Appl. No.: 13/288,591

(22) Filed: Nov. 3, 2011

(65) Prior Publication Data

US 2013/0113913 A1 May 9, 2013

(51) Int. Cl.
*G06K 9/00* (2006.01)

(52) U.S. Cl.
USPC .......................................................... 382/145

(58) Field of Classification Search
None
See application file for complete search history.

(56) References Cited

U.S. PATENT DOCUMENTS

| | | | |
|---|---|---|---|
| 5,070,401 A | 12/1991 | Salvati et al. | |
| 5,619,429 A | 4/1997 | Aloni et al. | |
| 5,774,212 A | 6/1998 | Corby | |
| 6,153,889 A | 11/2000 | Jones | |
| 6,362,875 B1 | 3/2002 | Burkley | |
| 6,424,733 B2 | 7/2002 | Langley | |
| 6,597,818 B2 * | 7/2003 | Kumar et al. | 382/294 |
| 7,099,078 B2 | 8/2006 | Spencer | |
| 7,489,811 B2 | 2/2009 | Brummel et al. | |
| 7,518,632 B2 | 4/2009 | Konomura | |
| 7,564,626 B2 | 7/2009 | Bendall et al. | |
| 7,619,728 B2 | 11/2009 | Ogburn et al. | |
| 7,656,445 B2 | 2/2010 | Heyworth | |
| 7,758,495 B2 | 7/2010 | Pease et al. | |
| 2002/0128790 A1 | 9/2002 | Woodmansee | |
| 2003/0063270 A1 | 4/2003 | Hunik | |
| 2004/0183900 A1 * | 9/2004 | Karpen et al. | 348/92 |
| 2004/0242961 A1 | 12/2004 | Bughici | |
| 2005/0016857 A1 | 1/2005 | Kovarsky et al. | |
| 2005/0129108 A1 | 6/2005 | Bendall et al. | |
| 2006/0050983 A1 | 3/2006 | Bendall et al. | |
| 2008/0298795 A1 * | 12/2008 | Kuberka et al. | 396/263 |
| 2011/0013846 A1 | 1/2011 | Hori | |
| 2011/0025844 A1 | 2/2011 | Hori | |
| 2011/0026805 A1 | 2/2011 | Hori | |

FOREIGN PATENT DOCUMENTS

WO   WO 2010/020338 A1   2/2010

OTHER PUBLICATIONS

Candès, Emmanuel J., et al. "Robust principal component analysis?." arXiv preprint arXiv:0912.3599 (2009).*

* cited by examiner

*Primary Examiner* — Stephen R Koziol
*Assistant Examiner* — Amandeep Saini
(74) *Attorney, Agent, or Firm* — Miller, Matthias & Hull LLP

(57) ABSTRACT

A system and method for performing automated defect detection of blades within an engine is disclosed. The system and method may include an image capture device capable of capturing and transmitting images of a plurality of blades of an engine, creating a normal blade model of an undamaged one of the plurality of blades and determining defects within the plurality of blades by utilizing the normal blade model.

20 Claims, 4 Drawing Sheets

SYSTEM AND METHOD FOR DATA-DRIVEN AUTOMATED BORESCOPE INSPECTION

TECHNICAL FIELD OF THE DISCLOSURE

The present disclosure relates to automated inspection techniques and, more particularly, relates to automated visual inspection techniques of images or videos captured by image capture devices such as borescopes.

BACKGROUND OF THE DISCLOSURE

Video inspection systems, such as borescopes, have been widely used for capturing images or videos of difficult-to-reach locations by "snaking" image sensor(s) to these locations. Applications utilizing borescope inspections include aircraft engine blade inspection, power turbine blade inspection, internal inspection of mechanical devices and the like.

A variety of techniques for inspecting the images or videos provided by borescopes for determining defects therein have been proposed in the past. Most such techniques capture and display images or videos to human inspectors for defect detection and interpretation. Human inspectors then decide whether any defect within those images or videos exists. These techniques are prone to errors resulting from human inattention. Some other techniques utilize automated inspection techniques in which most common defects are categorized into classes such as leading edge defects, erosion, nicks, cracks, or cuts and any incoming images or videos from the borescopes are examined to find those specific classes of defects. These techniques are thus focused on low-level feature extraction and to identify damage by matching features. Although somewhat effective in circumventing errors from human involvement, categorizing all kinds of blade damage defects within classes is difficult and images having defects other than those pre-defined classes are not detected.

Accordingly, it would be beneficial if an improved technique for performing defect detection were developed. It would additionally be beneficial if such a technique were automated, thereby minimizing human intervention and did not interpret defects based upon any categorization or classes.

SUMMARY OF THE DISCLOSURE

In accordance with one aspect of the present disclosure, a method of performing an automated defect detection is disclosed. The method may include providing an image capture device for capturing and transmitting data of an object, creating a normal model of the object; and performing an anomaly detection utilizing the normal model to determine defects within the object.

In accordance with another aspect of the present disclosure, a system for performing automated defect detection is disclosed. The system may include an image capture device for capturing and transmitting images of one or more blades of an engine, a monitoring and analysis site in at least indirect communication with the image capture device, and a monitoring and analysis site capable of creating a normal blade model and determining defects in the one or more blades of the engine.

In accordance with yet another aspect of the present disclosure, a method of performing automated defect detection is disclosed. The method may include providing an image capture device capable of capturing and transmitting images of a plurality of blades of an engine, creating a normal blade model of an undamaged one of the plurality of blades, and determining defects within the plurality of blades by utilizing the normal blade model.

While the present disclosure is susceptible to various modifications and alternative constructions, certain illustrative embodiments thereof will be shown and described below in detail. It should be understood, however, that there is no intention to be limited to the specific embodiments disclosed, but on the contrary, the intention is to cover all modifications, alternative constructions, and equivalents falling within the spirit and scope of the present disclosure.

DETAILED DESCRIPTION OF THE DISCLOSURE

Figure 1:
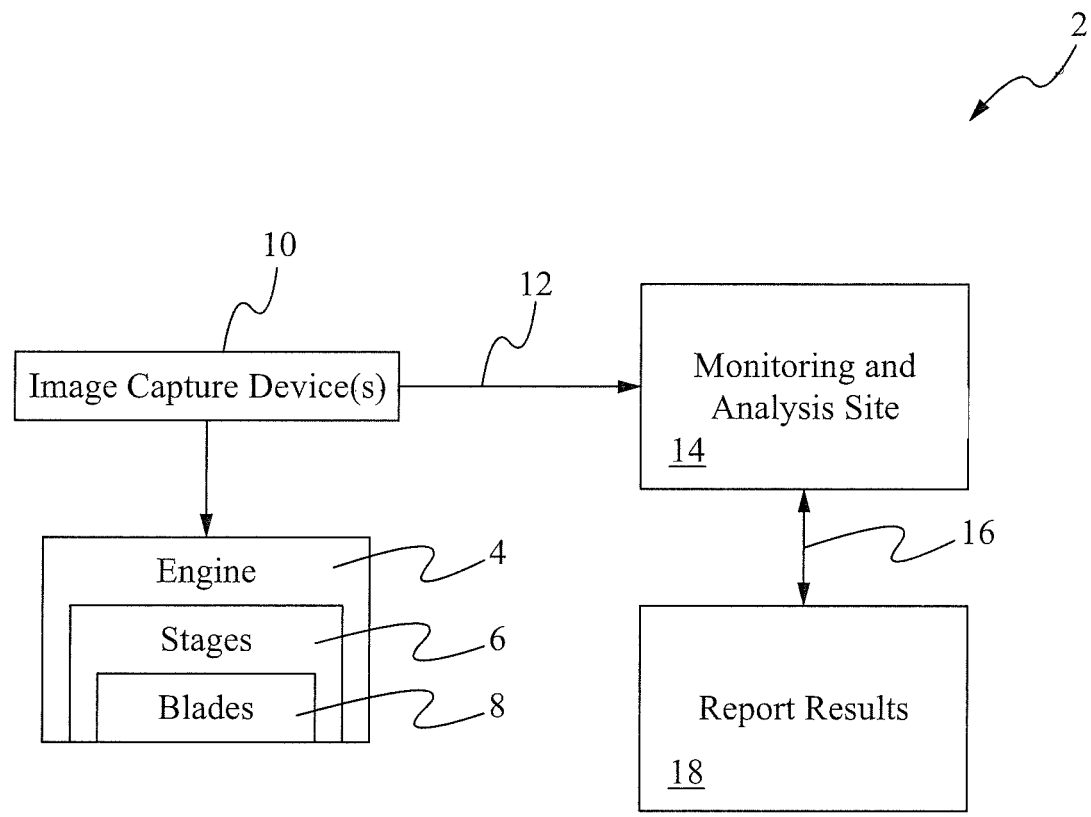
FIG. 1 is a schematic illustration of an automated defect detection system, in accordance with at least some embodiments of the present disclosure.

Referring to FIG. 1, a schematic illustration of an automated defect detection system 2 is shown, in accordance with at least some embodiments of the present disclosure. In at least some embodiments, the automated defect detection system 2 may be an automated borescope inspection (ABI) system. As shown, the automated defect detection system 2 may include an engine 4 having a plurality of stages 6, each of the stages having a plurality of blades 8, some or all of which may require visual inspection periodically, at predetermined intervals, or based on other criteria, by an image capture device 10. The engine may be representative of a wide variety of engines such as jet aircraft engines, aeroderivative industrial gas turbines, steam turbines, diesel engines, automotive and truck engines, and the like. Notwithstanding the fact that the present disclosure has been described in relation to visual inspection of the blades 8 of the engine 4, in other embodiments, the ABI system 2 may be employed to inspect other parts of the engine inaccessible by other means, as well as to perform inspection in other equipment and fields such as medical endoscope inspection, critical interior surfaces inspection in machined or cast parts, forensic inspection, inspection of civil structures such as buildings bridges, piping, etc.

The image capture device 10 may be an optical device having an optical lens or other imaging device or image sensor at one end and capable of capturing and transmitting images or videos through a communication channel 12 to a monitoring and analysis site 14. The image capture device 10 may be representative of any of a variety of flexible borescopes or fiberscopes, rigid borescopes, video borescopes or other devices such as endoscopes, which are capable of capturing and transmitting images or videos of difficult-to-reach areas through the communication channel 12. The communication channel 12 in turn may be an optical channel or alternatively may be any other wired, wireless or radio channel or any other type of channel capable of transmitting images and videos between two points including links involving the World Wide Web (www) or the internet.

With respect to the monitoring and analysis site 14, it may be located on-site near or on the engine 4, or alternatively it may be located on a remote site away from the engine. Furthermore, the monitoring and analysis site 14 may include one or more processing systems (e.g., computer systems having a central processing unit and memory) for recording, processing, and storing the images or videos received from the image capture device 10, as well as personnel for controlling operation of the one or more processing systems. Thus, the monitoring and analysis site 14 may receive the set of images or videos (referred hereinafter to as "data") of the blades 8 captured and transmitted by the image capture device 10 via the communication channel 12. Upon receiving the data, the monitoring and analysis site 14 may process that data to determine any defects within any of the blades 8. As will be described further below in FIG. 2, the defects may be determined by determining a normal model of an undamaged one of the blades 8 and comparing that normal model with the received data from the image capture device 10. Results (e.g., the defects) 18 may then be reported through communication channel 16. The results 18 may include information obtained by comparing the normal model and the data from the image capture device 10 and whether any defects in any of the blades 8.8 were found. Information about the type of defects, the location of the defect, size of the defect, etc. may also be reported as part of the results 18.

Similar to the communication channel 12, the communication channel 16 may be any of a variety of communication links including, wired channels, optical or wireless channels, radio channels or possibly links involving the World Wide Web (www) or the Internet. It will also be understood that although the results 18 have been shown as being a separate entity from the monitoring and analysis site 14, this need not always be the case. Rather, in at least some embodiments, the results 18 may be stored within and reported through the monitoring and analysis site 14 as well. Furthermore, reporting of the results 18 may involve storing the results in a database for future reference, as well as raising alarms when defects are detected.

Figure 2:
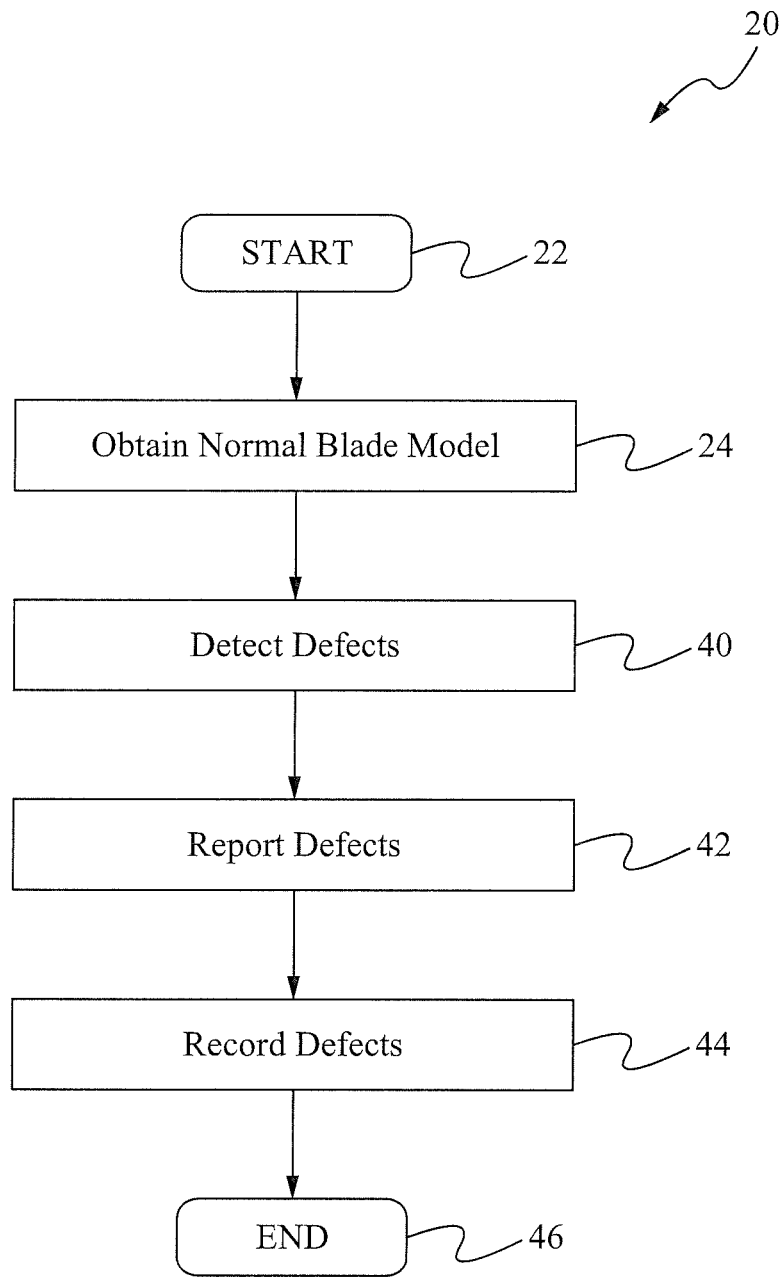
FIG. 2 is a flowchart showing steps of performing the automated defect detection using the automated defect detection system of FIG. 1.

Referring now to FIG. 2, a flowchart 20 showing sample steps which may be followed in performing the automated defect detection using the automated defect detection system 2 is shown, in accordance with at least some embodiments of the present invention. As shown, after starting at a step 22, the process proceeds to a step 24, where a normal model of the blades 8 is first obtained. The normal model may correspond to a model of an undamaged one of the blades 8 that may be utilized for determining defects in abnormal or damaged blades. A normal model for each of the stages 6 of the engine 4 may be created. Typically, all of the blades 8 in each of the stages 6 are similar, differing only between various stages. Thus, for each of the stages 6, one normal model of the blades 8 within that stage may be created and may be employed for determining defects in any of the blades within that stage.

The normal model may be created or otherwise learned automatically from the data transmitted by the image capture device 10 or, alternatively, the normal model may be created from data input by one or more users (e.g., personnel operating the engine 4, personnel controlling the monitoring and analysis site 14 or otherwise any entity having knowledge of the blades 8 within each of the stages 6). Each of the above techniques of creating the normal model is described in greater detail below.

Figure 3A:
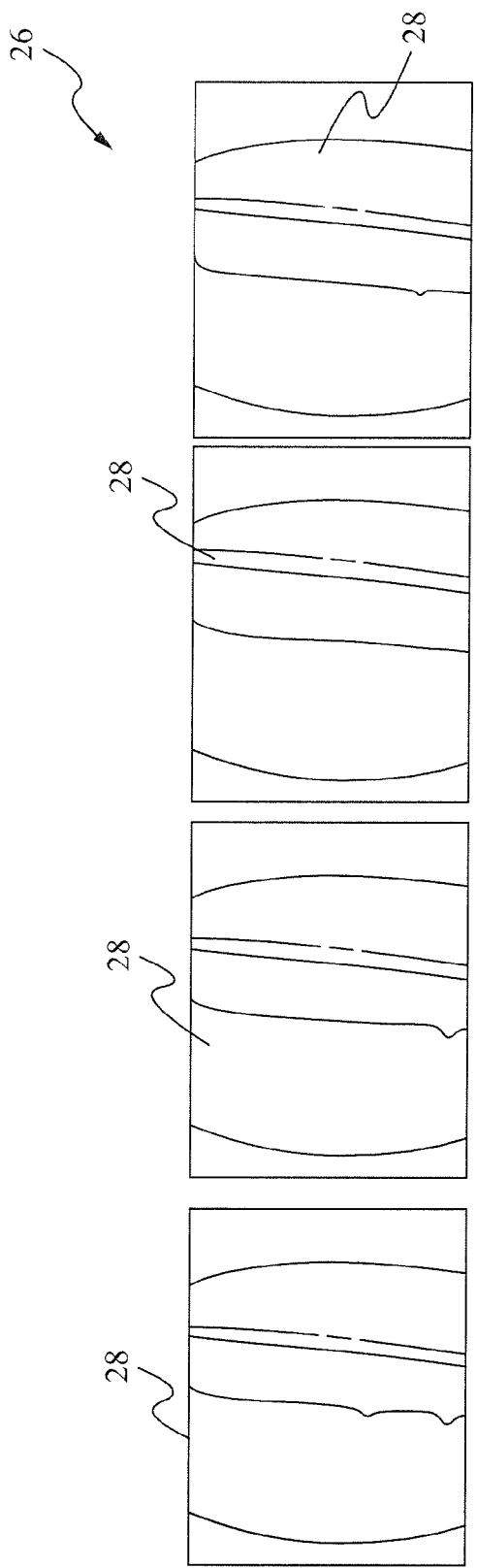
FIGS. 3a and 3b show a first exemplary technique of creating a normal model, in accordance with at least some embodiments of the present disclosure.
Figure 3B:
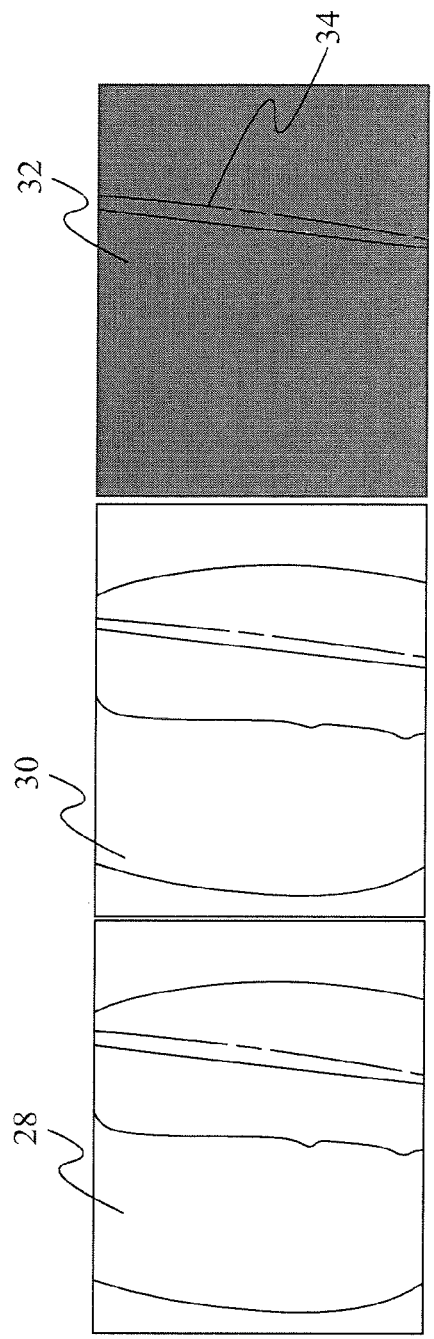

A first technique of creating the normal model is shown in FIGS. 3a and 3b. This first technique utilizes similar views from a set of the blades 8 to automatically learn and create the normal model. Specifically, as all of the blades 8 within each of the stages 6 are of the same size and geometry, when a second blade rotates to the same position (to obtain a similar view) as a first blade, images of the first and the second blade taken at that instant are almost the same. By performing mathematical operations on these images, the normal model may be learned, as well as the defects within those blades may be found.

Such similar views of the blades 8 may be obtained from a full or a partial turn of the engine 4, which may then be captured by the image capture device 10 and transmitted to the monitoring and analysis site 14 via the communication channel 12. It will be understood that one set (of similar views) may be obtained for each of the stages 6 for creating a normal model for that stage. Furthermore, all of the blades 8 within each of the stages 6 or, a subset of the blades within each of the stages may be employed for creating the set of blades with similar views. Upon receiving the set, each of the images within the set may then be decomposed into normal and abnormal regions, as explained below, and the normal regions may be selectively employed as the normal model.

Thus, FIG. 3a shows one set 26 of the blades 8 having similar views. Each image 28 within the set 26 corresponds to one of the blades 8 within one of the stages 6 of the engine 4. Notwithstanding the fact that in the present embodiment, four of the blades 8 have been employed for creating the set 26, in at least some other embodiments, the number of blades used may vary. Thus, in other embodiments, more than four of the blades 8 or possibly even less than four may be employed for obtaining the set 26. From the set 26, a normal model may be obtained by any of a variety of statistical techniques. In at least some embodiments, mathematical operations of a Robust Principal Component Analysis (RPCA) for obtaining the normal model may be employed. Using the Robust PCA technique, the set 26 may be decomposed into a low rank matrix and a sparse matrix. FIG. 3b shows one of the images 28 from the set 26, one column of low rank matrix 30 viewed as an image, which contains a normal model part or region, as well as a column of sparse matrix 32 viewed as an image, which contains anomalies or defects of that blade.

A particular one of the images 28 within the set 26 may be employed as a normal model only if the column of sparse matrix 32 corresponding to the particular image is empty. Accordingly, since the column of sparse matrix 32 shown in FIG. 3b is not empty (e.g., shows an anomaly 34 of the image 28), the image 28 may not be employed as the normal model. In case no column of the sparse matrix 32 is empty, any column in the low rank matrix may be considered as the normal model. Thus, by following the above RPCA procedure of obtaining a set of images of the blades 8 and by decomposing the images within that set into a normal and an abnormal part, the normal model may be automatically learned. One normal model for every one of the stages 6 of the engine 4 may be created.

A second technique for creating the normal model utilizes one or more user provided images such as three-dimensional images (3-D) or models or other user-selected data that may be employed to construct the normal model. As with the first technique, a normal model may be constructed (or learned) for every one of the stages 6 of the engine 4.

Figures 4A, 4B:
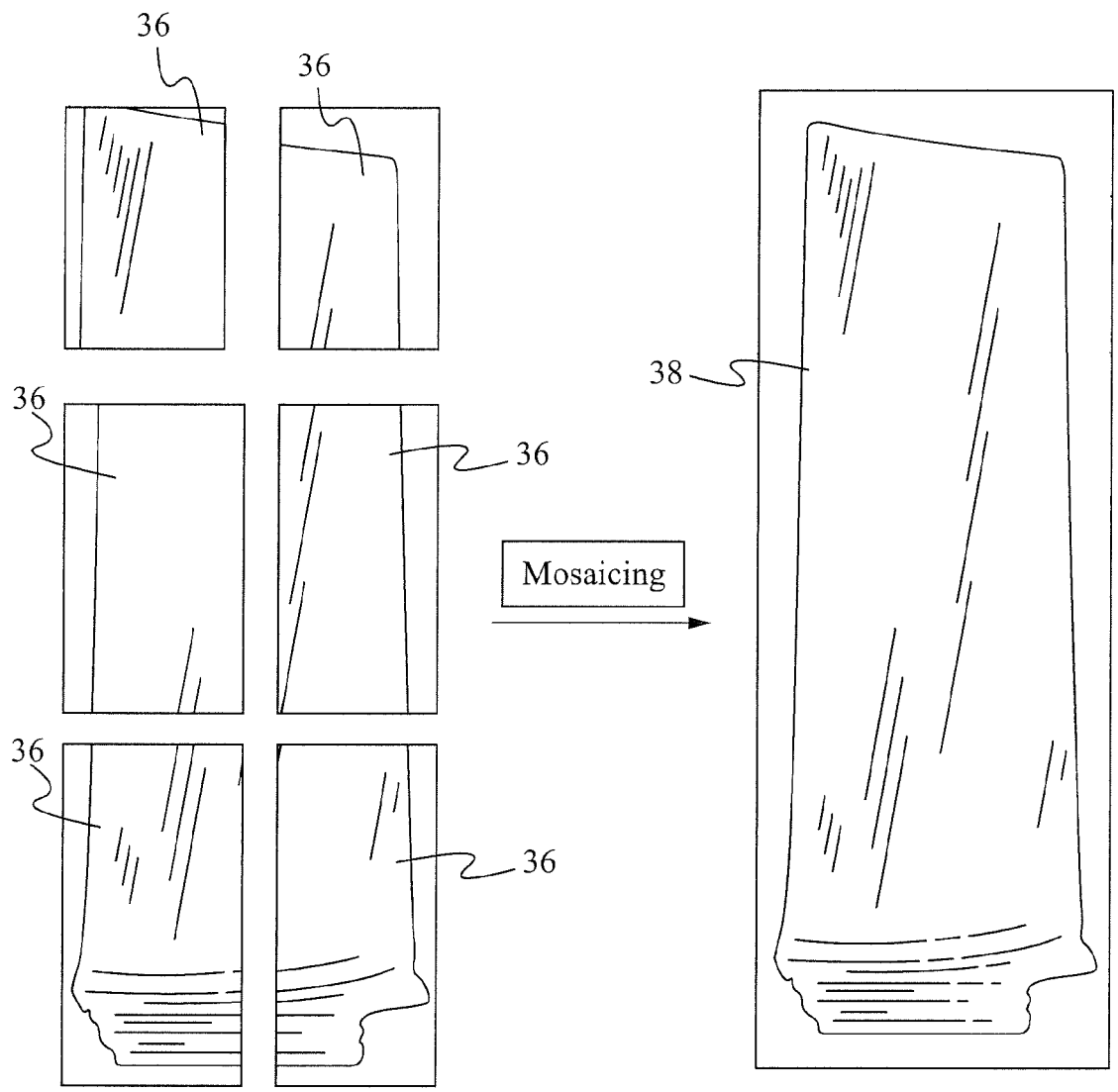
FIGS. 4a and 4b show a third exemplary technique of creating the normal model, in accordance with at least some other embodiments of the present disclosure.

A third technique for creating the normal model may be understood by referring to FIGS. 4a and 4b. The third technique may employ a mosaicing mechanism to construct the normal model when one view of the image capture device 10 may not capture the whole view of the blade. In the mosaicing technique, multiple views of one of the blades 8 and, particularly, one of the normal or undamaged blades may be obtained. Such multiple views of one of the blades 8 may be obtained by moving or turning the image capture device 10 around that particular blade. Thus, in contrast to the first technique in which similar views of multiple blades within each stage are obtained, in the third technique, multiple views of one single blade in each stage are obtained. FIG. 4*a* shows multiple images 36 of one of the blades 8 of one of the stages 6. The multiple images 36 may be captured and transmitted by the image capture device 10 via the communication channel 12 to the monitoring and analysis site 14. At the monitoring and analysis site 14, any of a variety of image mosaicing techniques may be employed to combine the multiple images 36 to obtain a normal model 38 of that blade, as shown in FIG. 4*b*. Similar to the first and the second techniques, one normal model per stage of the engine 4 may be created.

The third technique, which first obtains a complete blade image by mosaicing, may be combined with the first technique where the mosaiced images are first aligned using well known techniques such as Scale-Invariant Feature Transform (SIFT), Speeded Up Robust Feature (SURF), and RANdom SAmple Consensus (RANSAC), and then statistically analyzed, for example using the RPCA technique.

Returning now to FIG. 2, at the step 24, the normal model of the blades 8 may be created utilizing one of the first, second or the third techniques described above. The normal model created may be monitored at the monitoring and analysis site 14 to ensure the quality and completeness of the obtained normal model. In at least some embodiments, an evidence grid for ensuring that no gaps exist within the input model data (e.g., the multiple images 36 of the third technique) may be employed. In other embodiments, other mechanisms for monitoring the normal model may be used.

Upon obtaining the normal model, defects within any of the blades within a particular one of the stages 6 corresponding to the normal model of the step 24 may be obtained at a step 40. Defects may be detected by comparing any current view or current image of one of the blades 8 received from the image capture device 10 with the normal model of that stage. Comparisons between the current view image and the normal model may be performed by aligning the field of view (FOV) thereof and determining the difference between the two (the current view image and the normal model). Simultaneous image segmentation and 3D pose estimation techniques may be employed to align the FOV of the current view image and the normal model. If the difference detected between the current view image and the normal model is over a pre-determined threshold value, a defect within that blade (e.g., the blade corresponding to the current view image) is determined. It will be understood that the current view image and the normal blade may be compared only if both the images correspond to the same stage 6.

Furthermore, the comparison may be performed to determine the type of defects such as leading edge defects, erosions, nicks, dents, cracks or cuts, the location of the defects, the size of the defects, and other defect parameters. After finding any defects at the step 40, those defects may be reported at a step 42. As discussed above, reporting the defects may involve raising alarms to alert personnel to replace or fix the defective blade before operation. In addition to reporting the defects at the step 42, the defects may also be recorded into a database at a step 44 for future reference. The process then ends at a step 46.

Industrial Applicability

In general, the present disclosure sets forth a system and method for performing automated defect detection. The system and method may include providing an image capture device for capturing and transmitting images of blades of an engine to a monitoring and analysis site. Using the information exported by the image capture device, a normal model (e.g., a normal blade model) of the blades for each stage of the engine may be created or automatically learned. Defects in the blades may be detected by utilizing the normal model and, particularly, by comparing the images of the blades with the normal model. The method may also include applying the described process to other component(s) or mechanical systems.

By virtue of comparing a current view image of the blade or component with a normal model image, the present disclosure provides for an automated visual inspection using automatic image analysis in which human involvement is minimized, thereby minimizing human related errors and improving inspection reliability and speed. Also, the present disclosure teaches defect detection using an anomaly detection process, as opposed to looking for certain specific types of defects and categorizing those defects within classes as taught by conventional mechanisms. Accordingly, the present disclosure teaches identifying all types of defects, instead of looking for pre-defined ones.

While only certain embodiments have been set forth, alternatives and modifications will be apparent from the above description to those skilled in the art. These and other alternatives are considered equivalents and within the spirit and scope of this disclosure and the appended claims.

What is claimed is:

1. A method of performing automated defect detection, the method comprising:
    providing an image capture device for capturing and transmitting video images of an object in motion inside of a device;
    creating a normal model of the object by performing Robust Component Analysis on the video images to simultaneously decompose the video images into a low rank matrix representing a normal object and a sparse matrix representing an object anomaly; and
    performing an anomaly detection utilizing the normal model to determine defects within the object.

2. The method of claim 1, wherein creating the normal model of the object comprises:
    providing a series of images with similar views of the object;
    performing a Robust Principal Component Analysis of the series of images to obtain the normal model.

3. The method of claim 2, wherein performing the Robust Principal Component Analysis comprises:
    utilizing one of (a) one of the series of images for the normal model if the sparse matrix corresponding to at least one of the series of images is empty; and (b) the low rank component of one of the series of images for the normal model if the sparse matrix corresponding to the series of images is not empty.

4. The method of claim 1, wherein creating the normal model of the object comprises:
    providing multiple views of an undamaged one of the object; and
    mosaicing the multiple views to obtain the normal model.

5. The method of claim 1, wherein creating the normal model of the object comprises creating the normal model from a plurality of user input images.

6. The method of claim 1, wherein the object is a plurality of blades within one stage of at least one of an engine and a turbine.

7. The method of claim 1, wherein performing an anomaly detection comprises:
   aligning a field of view of the normal model and a current view image of the object;
   comparing the normal blade and the current view image of the object to determine differences therebetween; and
   identifying a defect if the differences between the normal model and the current view image is beyond a threshold value.

8. The method of claim 7, further comprising raising an alarm when the defect is identified.

9. The method of claim 8, further comprising recording the defect for future reference.

10. A system for performing automated defect detection, the system comprising:
   an image capture device for capturing and transmitting video images of one or more moving components of an object; and
   a monitoring and analysis site in at least indirect communication with the image capture device, the monitoring and analysis site capable of creating a normal component model using Robust Component Analysis on the video images to simultaneously decompose the video images into a low rank matrix representing a normal component and a sparse matrix representing a component anomaly, and determining defects in the one or more components of the object.

11. The system of claim 10, wherein the object is one of an engine and a turbine.

12. The system of claim 11, wherein each of the engine and the turbine comprises a plurality of stages, each of the plurality of stages having a plurality of similar blades.

13. The system of claim 10, wherein the monitoring and analysis site is at least one of a remote site and an on-site.

14. A method of performing automated defect detection, the method comprising:
   providing an image capture device capable of capturing and transmitting video images of a plurality of rotating blades of an engine;
   creating a normal blade model of an undamaged one of the plurality of blades using Robust Principal Component Analysis on the video images to simultaneously decompose the video images into a low rank matrix representing a normal blade and a sparse matrix representing a blade anomaly; and
   determining defects within the plurality of blades by utilizing the normal blade model.

15. The method of claim 14, wherein determining defects comprises determining one or more of a type of the defect, a location of the defect and a size of the defect.

16. The method of claim 15, wherein the type of the defect may be one or more of leading edge defects, erosions, nicks, cracks, dents and cuts.

17. The method of claim 14, wherein creating the normal blade model comprises:
   obtaining a set having images of the plurality of blades; and
   utilizing at least one of the normal part as the normal blade model if the abnormal part is empty, and utilizing the low rank matrix for the normal blade model if the abnormal part is not empty.

18. The method of claim 17, wherein the set is obtained from a full or partial turn of the engine.

19. The method of claim 14, wherein one of the normal blade model is obtained for each stage within the engine.

20. The method of claim 14, wherein creating the normal blade model comprises:
   obtaining multiple view images of a normal one of the plurality of blades;
   mosaicing the multiple view images into the normal blade model.

* * * * *